United States Patent
Kroll

(12) 
(10) Patent No.: US 7,181,269 B1
(45) Date of Patent: Feb. 20, 2007

(54) IMPLANTABLE DEVICE THAT DIAGNOSES ISCHEMIA AND MYOCARDIAL INFARCTION AND METHOD

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 75 days.

(21) Appl. No.: 10/823,427

(22) Filed: Apr. 12, 2004

(51) Int. Cl.
*A61B 5/0472* (2006.01)
*A61N 1/37* (2006.01)

(52) U.S. Cl. .................. 600/517; 600/515; 607/18; 607/25

(58) Field of Classification Search ............ 600/481, 600/483, 515, 517; 607/18, 25, 26
See application file for complete search history.

(56) References Cited

U.S. PATENT DOCUMENTS

| | | | |
|---|---|---|---|
| 5,199,428 A | 4/1993 | Obel et al. | 128/419 C |
| 5,273,049 A * | 12/1993 | Steinhaus et al. | 600/508 |
| 5,313,953 A | 5/1994 | Yomtov et al. | 128/696 |
| 5,388,578 A | 2/1995 | Yomtov et al. | 128/642 |
| 6,021,350 A | 2/2000 | Mathson | 607/17 |
| 6,115,630 A | 9/2000 | Stadler et al. | 600/521 |
| 6,128,526 A | 10/2000 | Stadler et al. | 600/517 |
| 6,368,284 B1 | 4/2002 | Bardy | 600/508 |
| 6,381,493 B1 | 4/2002 | Stadler et al. | 607/9 |
| 6,397,100 B2 | 5/2002 | Stadler et al. | 600/509 |
| 6,424,860 B1 * | 7/2002 | Karlsson et al. | 600/512 |
| 6,466,821 B1 | 10/2002 | Pianca et al. | 607/18 |
| 6,501,983 B1 | 12/2002 | Natarajan et al. | 600/517 |
| 6,514,195 B1 * | 2/2003 | Ferek-Petric | 600/17 |
| 6,604,000 B2 | 8/2003 | Lu | 607/17 |
| 6,609,023 B1 | 8/2003 | Fischell et al. | 600/515 |
| 2002/0016548 A1 | 2/2002 | Stadler et al. | 600/509 |
| 2002/0072777 A1 | 6/2002 | Lu | 607/17 |
| 2002/0143262 A1 | 10/2002 | Bardy | 600/508 |
| 2003/0013974 A1 | 1/2003 | Natarajan et al. | 600/481 |
| 2003/0023175 A1 * | 1/2003 | Arzbaecher et al. | 600/509 |
| 2003/0045805 A1 | 3/2003 | Sheldon et al. | 600/513 |
| 2003/0045908 A1 | 3/2003 | Condie et al. | 607/9 |
| 2003/0139778 A1 | 7/2003 | Fischell et al. | 607/3 |
| 2004/0122478 A1 * | 6/2004 | Stadler et al. | 607/17 |

FOREIGN PATENT DOCUMENTS

| | | |
|---|---|---|
| EP | 0 529 055 B1 | 5/1997 |
| EP | 0 879 618 A1 | 11/1998 |

* cited by examiner

*Primary Examiner*—Robert E. Pezzuto
*Assistant Examiner*—Tammie K. Heller

(57) ABSTRACT

An implantable device detects and discriminates between ischemia and myocardial infarction. The device includes a plurality of electrodes that provide a plurality of cardiac activity sensing electrode configurations. A sensing circuit provides a plurality of electrograms in response to cardiac activity sensed by the electrode configurations. A discriminator detects and discriminates between ischemia and myocardial infarction responsive to ST segments of the electrograms. The device may further discriminate an equivocal condition and initiate a secondary analysis for diagnosing spasm, anxiety, or exercised induced ischemia.

18 Claims, 9 Drawing Sheets

IMPLANTABLE DEVICE THAT DIAGNOSES ISCHEMIA AND MYOCARDIAL INFARCTION AND METHOD

FIELD OF THE INVENTION

The present invention generally relates to an implantable device and method that detects and discriminates between ischemia and myocardial infarction of a human heart. The present invention is more particularly directed to such an implantable device which takes the form of an implantable cardiac stimulation device.

BACKGROUND

Many patients that suffer what is commonly called a heart attack have a myocardial infarction. Myocardial infarction is a necrosis of cardiac tissue brought on by a reduction in blood flow to the infarcted area caused by either a chronic obstruction in an artery or an acute obstruction such as a thrombus in the artery. Hence, myocardial infarction is a total blockage of a cardiac artery.

Ischemia (I) of a heart also results in decreased blood flow, but not as pronounced. It is caused by a partial blockage of an artery and, in many cases, leads to a myocardial infarction.

Both ischemia and myocardial infarction are conditions which are desirably found at an early stage. This is true especially for a myocardial infarction as a heart attack could be eminent. Unfortunately, many people fail to seek prompt treatment for myocardial infarction (MI) until it is too late because most causes of chest pain are not cardiac related.

To monitor patients for ischemia and myocardial infarction, physicians may rely upon periodic EKGs (electrocardiograms) which generally require as many as ten leads to be attached to the patient. In addition, after the EKG, physicians then generally require the patient to take a stress test wherein the patient is caused to run on a treadmill until the patient is essentially exhausted to stress the heart. During and after the treadmill exercise the twelve lead EKG is used to determine if the heart continues to receive adequate blood supply while under the stress conditions. Obviously such monitoring is inconvenient to the patient. Physicians may also rely upon Holtor monitoring recordings which may last from 24 to 48 hours. These additional monitoring techniques are equally as inconvenient and in addition, are also annoying. Since all of these monitoring techniques can, at best, only be administered periodically as a practical matter, and because episodes of myocardial infarction are unpredictable events, all too often, a myocardial infarction is not detected until the patient has already experienced heart damage.

From the foregoing, it can be seen that for some patients, it is very desirable to monitor for ischemia and myocardial infarction. Many of these patients will already have an implanted cardiac stimulation device such as a pacemaker or a combined pacemaker and defibrillator.

Implantable cardiac devices have been proposed in the art for detecting and monitoring ischemia. Many of these devices may be solely for monitoring or incorporated into pacemakers and defibrillators. With modern day storage technology and telemetry, these devices are capable of collecting and communicating large amounts of ischemia data. Unfortunately, these prior devices are incapable of distinguishing between ischemia and the more serious condition of myocardial infarction.

SUMMARY

What is described herein is an implantable device that detects and discriminates between ischemia and myocardial infarction of a patient's heart. The device comprises a plurality of electrodes that provide a plurality of cardiac activity sensing electrode configurations, a sensing circuit that provides a plurality of electrograms in response to cardiac activity sensed by the electrode configurations, and a discriminator that detects and discriminates between ischemia and myocardial infarction responsive to ST segments of the electrograms. The device may be, for example, an implantable cardiac stimulation device.

The discriminator is preferably responsive to positive ST segments of the electrograms with respect to a baseline and negative ST segments of the electrograms with respect to a baseline to detect myocardial infarction and ischemia respectively.

The device may further comprise a summer that provides a sum of the absolute value of the electrograms. The discriminator may then be responsive to the electrogram absolute value sum to detect ischemia and myocardial infarction.

The device may further comprise a divider that divides the electrogram absolute value sum by an amplitude of one of the electrograms to provide a normalized value. The discriminator may then detect myocardial infarction and ischemia when the normalized value exceeds a predetermined value. The amplitude of one of the electrograms may, for example, be an R wave amplitude.

The device may further comprise a summer that provides a sum of ST segments of the electrograms and a divider that provides a normalized ST segment value from the ST segment sum. The discriminator may then detect myocardial infarction when the normalized ST segment value is greater than a first value and detects ischemia when the normalized ST segment value is less than a second value.

The discriminator may discriminate between an ischemic condition of the heart, a myocardial infarcted condition of the heart, and an equivocal condition of the heart. An arithmetic logic unit may be employed to provide an electrogram value of the electrograms. The discriminator may then detect myocardial infarction when the electrogram value is greater than a first value, ischemia when the electrogram value is less than a second value, and the equivocal condition when the electrogram value is between the first and second values.

The discriminator may provide a secondary analysis in response to detecting an equivocal condition. The secondary analysis may include measurement of one of patient heart rate, physical activity, and posture. The discriminator may detect and discriminate between the conditions of spasm, anxiety, and exercised induced ischemia during the secondary analysis. If ischemia is detected, the discriminator preferably then determines an ischemia burden. The ischemia burden may be proportional to the duration of the ischemia.

In one illustrative embodiment, an implantable device comprises a plurality of electrodes that provide a plurality of cardiac activity sensing electrode configurations, a sensing circuit that provides a plurality of electrograms in response to cardiac activity sensed by the electrode configurations, a summer that provides a sum of ST segments of the electrograms, and a divider that provides a normalized ST segment value from the ST segment sum. The device further comprises a discriminator that detects myocardial infarction when the normalized ST segment value is greater than a first value and that detects ischemia when the normalized ST segment value is less than a second value.

In another illustrative embodiment, an implantable device is disclosed that detects and discriminates between conditions of a patient's heart. The device comprises a plurality of electrodes that provide a plurality of cardiac activity sensing electrode configurations, a sensing circuit that provides a plurality of electrograms in response to cardiac activity sensed by the electrode configurations, and a discriminator that detects and discriminates between an ischemic condition of the heart, a myocardial infarcted condition of the heart, and an equivocal condition of the heart. The discriminator provides a secondary analysis in response to detecting an equivocal condition.

In another embodiment, a method is disclosed for detecting and discriminating between ischemia and myocardial infarction of a patient's heart. The method comprises sensing cardiac activity of the heart with a plurality of cardiac activity sensing electrode configurations to provide a plurality of electrograms, and discriminating between ischemia and myocardial infarction of the heart responsive to ST segment changes in the electrograms.

BRIEF DESCRIPTION OF THE DRAWINGS

Further features and advantages may be more readily understood by reference to the following description taken in conjunction with the accompanying drawings, in which.

DESCRIPTION OF THE PREFERRED EMBODIMENTS

The following description is of the best mode presently contemplated. This description is not to be taken in a limiting sense but is made merely for the purpose of describing the general principles of the illustrative embodiments. The scope of the invention should be ascertained with reference to the issued claims. In the description that follows, like numerals or reference designators will be used to refer to like parts or elements throughout.

Figure 1:
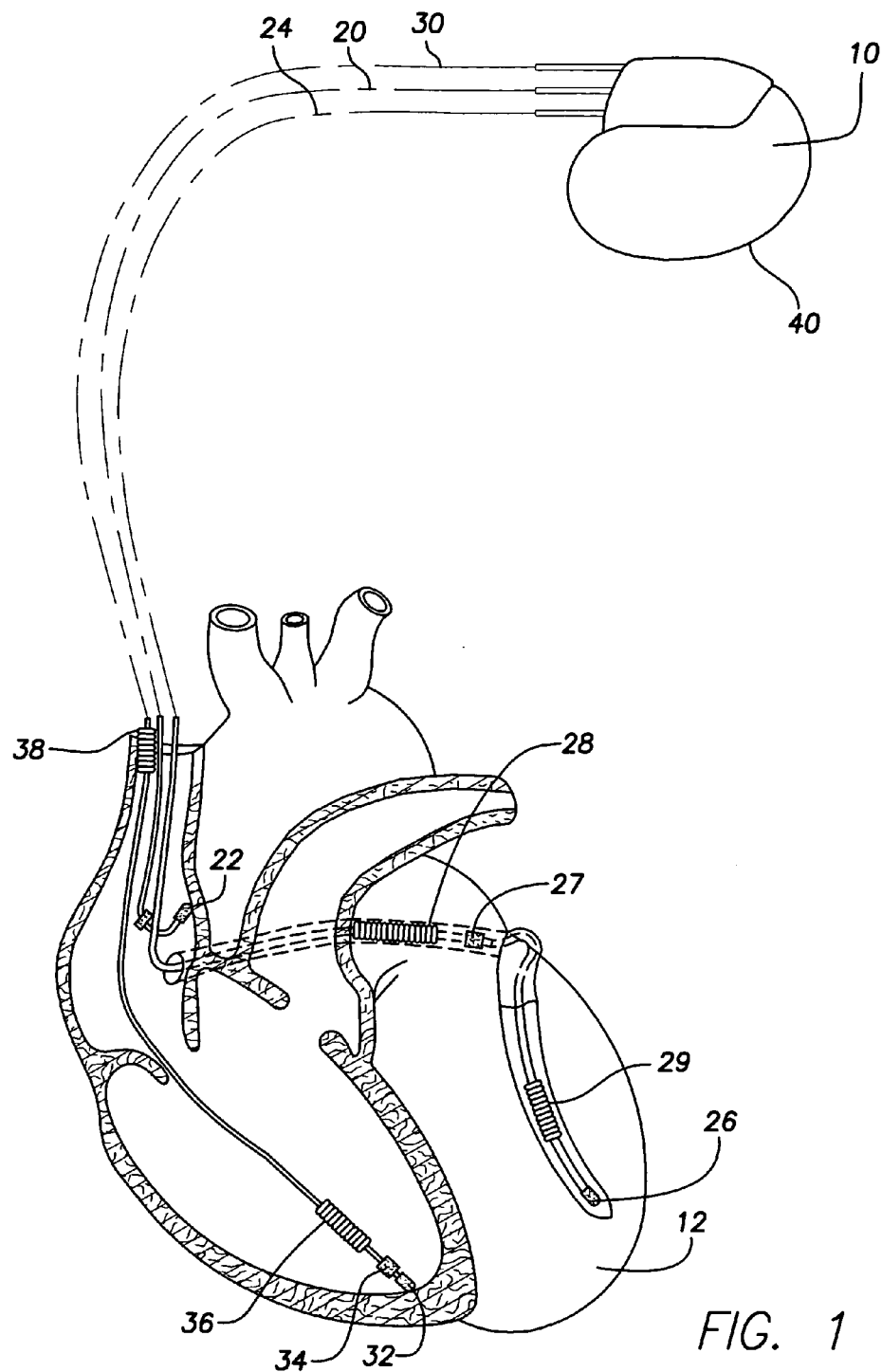
FIG. 1 is a simplified diagram illustrating an implantable stimulation device in accordance with one illustrative embodiment.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing and shock therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left ventricular shocking therapy using a left ventricular coil electrode 29, left atrial pacing therapy using at least a left atrial ring electrode 27, and left atrial shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
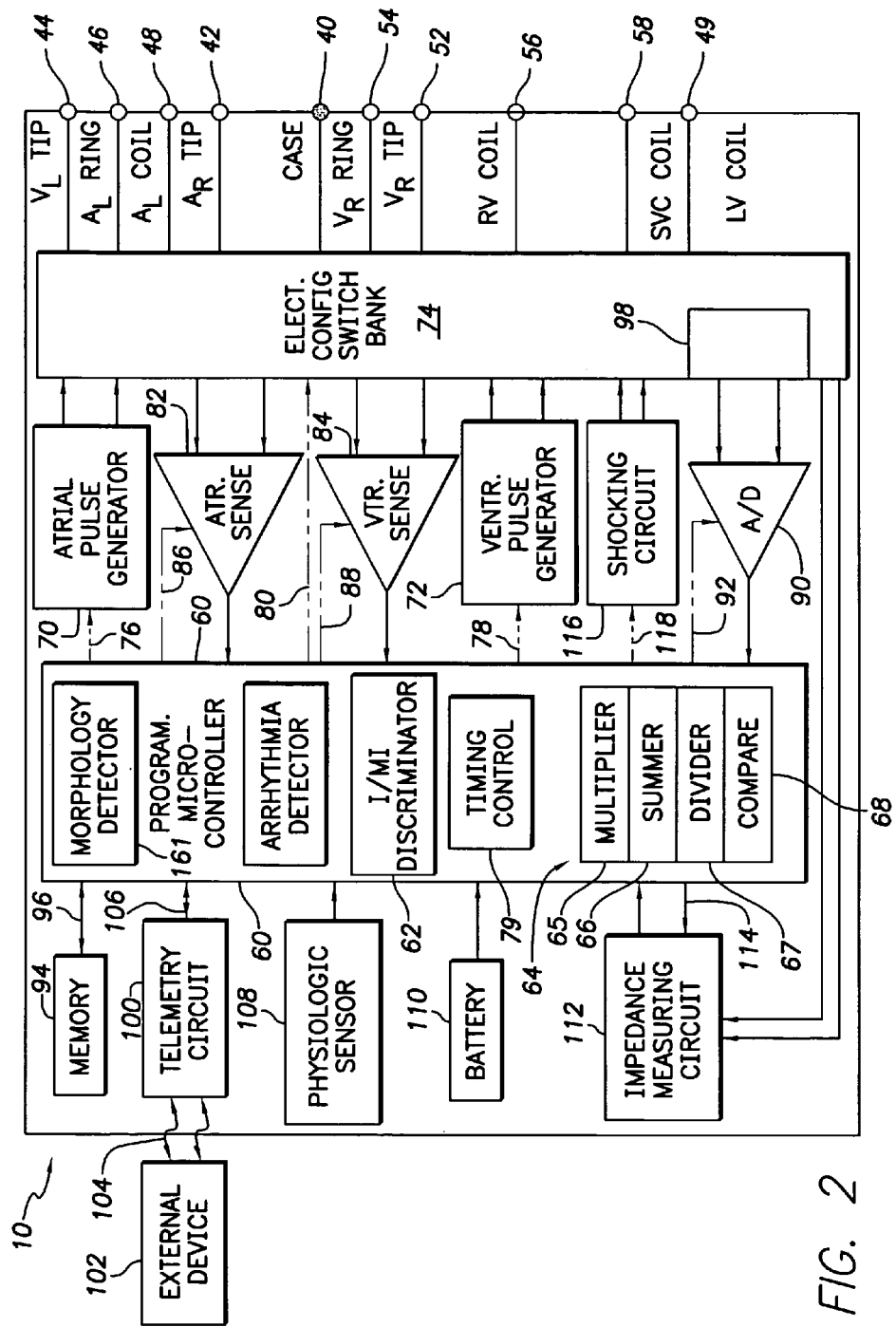
FIG. 2 is a functional block diagram of the implantable stimulation device of FIG. 1 illustrating an illustrative embodiment.

As illustrated in FIG. 2, a simplified block diagram is shown of the implantable stimulation device 10 according to one illustrative embodiment. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation while also providing detection of a discrimination between ischemia and MI according to one illustrative embodiment. Still further, as one of ordinary skill may appreciate, the illustrative embodiments may be practiced with a device dedicated to detection and I/MI discrimination only without providing any stimulation therapy.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes or sensing purposes in accordance with this embodiment. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left ventricular shocking terminal ($L_V$ COIL) 49 a left atrial ring terminal ($A_L$ RING) 46, and a left atrial shocking terminal ($A_L$ COIL) 48, which are adapted for connection to the left ventricular ring electrode 26, the left ventricular coil electrode 29, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., and heart rate (HR) which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes including the case 40 of the device 10.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The physiologic sensor 108 may further include a posture sensor. The posture sensor may detect the posture of the patient between a fully upright position and a supine position. To that end, the posture sensor may include accelerometers which detect acceleration in three mutually transverse directions. The signals from the posture sensor may be provided to a control circuit to generate different control signals. A first control signal may be a logical "1" if the patient is in an upright position and a logical "0" if the patient is in a supine position. A second control signal may be a multiple-bit binary fractional factor between 0 and 1 representing the posture of the patient. For example, the fractional factor may vary from 0, representing the patient in a supine position, to 1, representing the patient in a fully upright position. One such posture sensor is fully described in U.S. Pat. No. 6,466,821 to Pianca et al., titled "AC/DC Multi Axis Accelerometer for Determining Patient Activity and Body Position," which patent is owned by the assignee of the present invention and incorporated herein in its entirety by reference.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries.

As further shown in FIG. 2, the device 10 is shown as having an impedance measuring circuit 112 which is enabled by the microcontroller 60 via a control signal 114. The impedance measuring circuit 112 is not critical and is shown only for completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

In accordance with this embodiment, and with further reference to FIG. 2, it will be noted that the device 10 includes a discriminator 62. The discriminator 62, in accordance with one illustrative embodiment, is capable of both detecting ischemia (I) and a myocardial infarction (MI) and discriminate between ischemia and myocardial infarction. In order to support the discriminator 62, in accordance with this embodiment, the device 10 further includes an arithmetic logic unit (ALU) 64. The arithmetic logic unit 64 includes a multiplier 65, a summer 66, a divider 67, and a comparer 68.

In order to detect and discriminate ischemia and myocardial infarction, the device 10 utilizes a plurality of sensing electrode configurations to generate a like plurality of electrograms (EGMs). In accordance with this embodiment, the sensing electrode configurations may include a first configuration including the left ventricular coil electrode 29 and right atrial coil electrode 38, a second electrode configuration including the left ventricular coil electrode 29 and the right ventricular coil electrode 36, and a third electrode configuration including the enclosure 40 of the device 10 and the left ventricular coil electrode 29. The coil electrodes are utilized for this purpose because they represent large electrodes which will provide reliable sensing of ST segment changes since such electrodes have a better low frequency response and provide wider peripheral sensing or larger global heart area than provided by smaller electrodes such as, for example, pacing electrodes. The left ventricular coil electrode 29, right atrial coil electrode 38, right ventricular coil electrode 36, and the device enclosure or can 40 are selected to provide a global view of the heart. The difference in diagnostic capability of these electrode configurations will be described subsequently with reference to FIGS. 11–13.

The electrograms generated by the foregoing electrode configurations are generated by the data acquisition system 90, digitized, and stored in memory 94. The electrograms are then processed in a manner to be described subsequently to enable the detection and discrimination between ischemia and myocardial infarction. In addition, a third condition hereinafter referred to as an equivocal condition may also be determined by the discriminator 62 and prompt a second or secondary diagnosis to be described hereinafter. The results of all diagnoses may be stored in memory 94 for later access by the physician through the telemetry circuit 100 and signal a suitable alarm to the patient, when required, advising the patient to contact the patient's physician.

Figure 3:
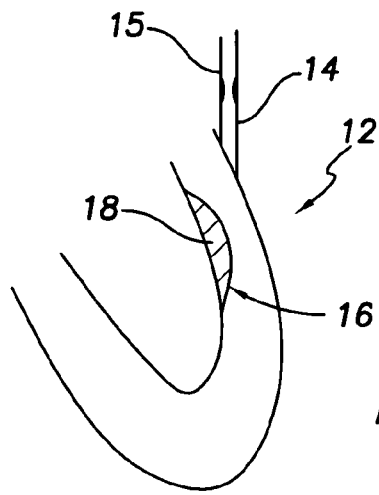
FIG. 3 is a simplified partial sectional view of a heart illustrating a subendocardial ischemia of a heart and a partially occluded coronary artery.

Referring now to FIG. 3, it provides a simplified partial sectional view of the heart 12. Here it may be seen that in spite of a lesion 15, there is less than total blockage of the coronary artery 14. Frequently, this becomes significant when the patient exercises. As may be further noted in FIG. 3, there is ischemia in the subendocardium 16 shown by the lined area 18. Since there is ischemia only in the subendocardium, there is sufficient pressure, in spite of the lesion in the coronary artery 14, to provide adequate blood support to the subepicardium.

Figure 4:
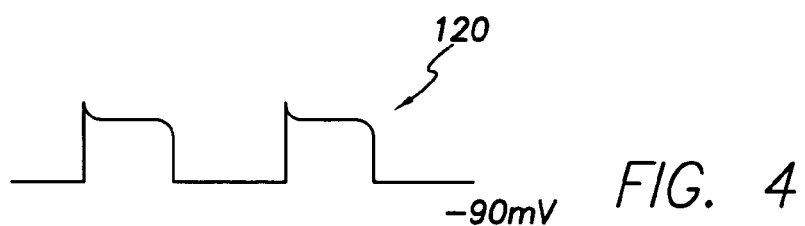
FIG. 4 is an electrogram (EGM) signal of the subepicardium shown in FIG. 3.

FIG. 4 shows an electrogram signal of the subepicardium. In spite of the lesion 15 in the coronary artery 14, the subepicardium is adequately profused. Hence, as will be noted in FIG. 4, the electrogram signal 120 has a normal activation potential with a resting potential going down to −90 mV. This resting potential is in the normal range.

Figure 5:
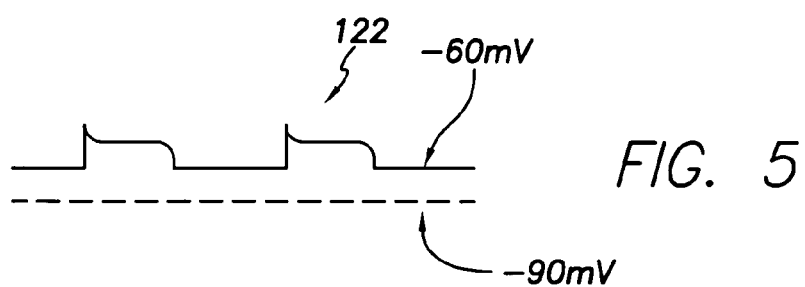
FIG. 5 is an EGM signal corresponding to the subendocardial ischemia shown in FIG. 3.

FIG. 5 shows an electrogram signal 122 corresponding to the subendocardial ischemia shown in FIG. 3. The ischemic subendocardial cells 18 result in a decreased resting potential of, for example, −60 mV.

Figure 6:
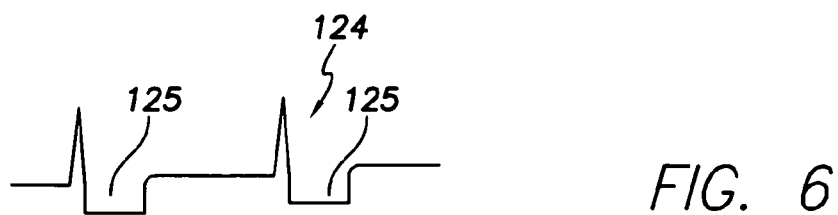
FIG. 6 is an EGM signal corresponding to the potential difference across the heart by virtue of the subendocardial ischemia of FIG. 3.

FIG. 6 shows an electrogram signal 124 representing the potential difference across the heart by virtue of the subendocardial ischemia of FIG. 3. This difference is technically a TQ elevation but will appear as an ST depression because of AC coupling of cardiac activity sense amplifiers. Hence, as will be noted in FIG. 6, an ST depression as, for example, ST depressions 125 of FIG. 6, typically evidence an ischemic attack.

Figure 7:
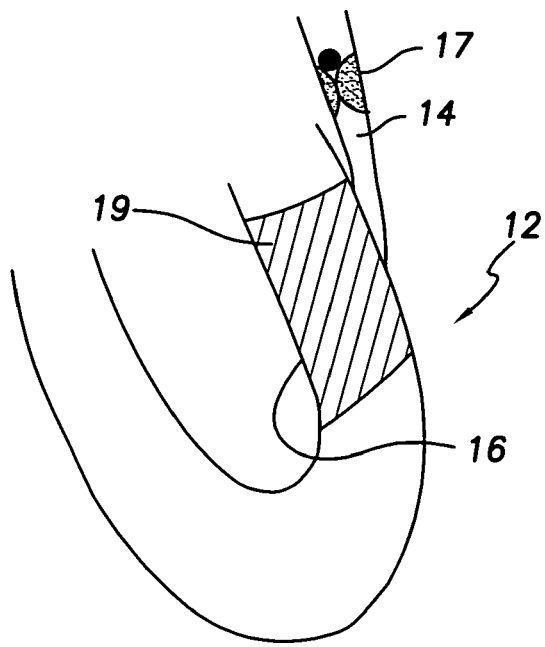
FIG. 7 is a simplified partial sectional view of the heart of FIG. 3 but illustrating a subepicardial myocardial infarction and a subendocardial myocardium infarction of the heart.

FIG. 7 is a simplified partial sectional view of the heart showing a total occlusion 17 within the coronary artery 14 and a total occlusion 19 in the endocardium 16. This is the typical situation with a myocardial infarction.

Figure 8:
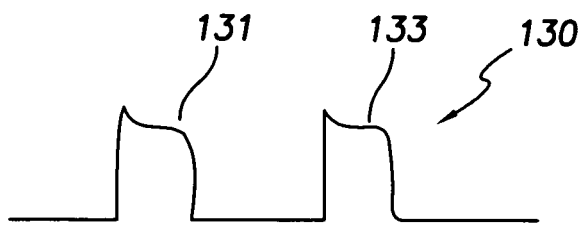
FIG. 8 is an EGM signal corresponding to the subepicardial myocardial infarction (MI) shown in FIG. 7.
Figure 9:
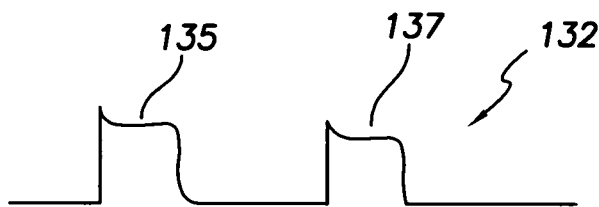
FIG. 9 is an EGM signal corresponding to the subendocardial myocardial infarction (MI) shown in FIG. 7.
Figure 10:
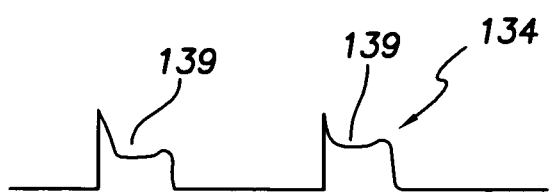
FIG. 10 is an EGM signal corresponding to the potential difference across the heart by virtue of the subepicardial MI and the subendocardial MI of FIG. 7.

FIG. 8 is an electrogram signal 130 corresponding to the subepicardial myocardial infarction shown in FIG. 7 and FIG. 9 is an electrogram signal 132 corresponding to the subendocardial myocardial infarction shown in FIG. 7. It may be noted that the subendocardial electrogram signal is similar to that seen in the ischemic condition of FIG. 3. However, while the resting potential may be decreased in the subepicardial tissue, the voltages in phases 131 and 133 are not decreased in the subepicardial electrogram 130 as much as the corresponding phases 135 and 137 of the electrogram 132 of the subendocardium. As a result, as will be seen in the electrogram 134 of FIG. 10, the potential difference across the heart during the activation potentials corresponding to phases 131, 133, 135, and 137 correlate to a decreased potential difference of the ST regions which, by virtue of the aforementioned AC coupling of the sense amplifiers, appears in the electrogram 134 as an ST elevation.

From the foregoing, it will be seen that an ST depression is therefore associated with an ischemic attack and an ST elevation is associated with myocardial infarction. This distinction, as will be seen hereinafter, is utilized to advantage in discriminating between ischemia and myocardial infarction in accordance with this embodiment.

Figure 11:
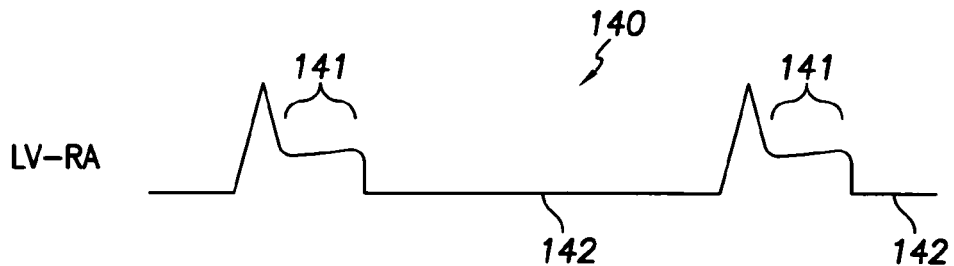
FIG. 11 is an EGM signal resulting from a left ventricular MI as sensed between a left ventricular electrode and a right atrial electrode.
Figure 12:
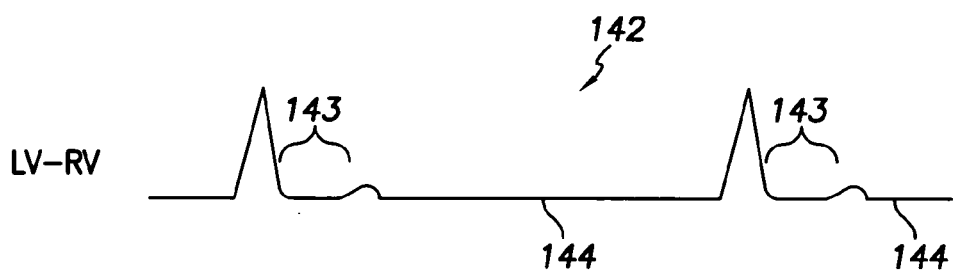
FIG. 12 is an EGM signal resulting from the left ventricular MI as sensed between a left ventricular electrode and a right ventricular electrode.
Figure 13:
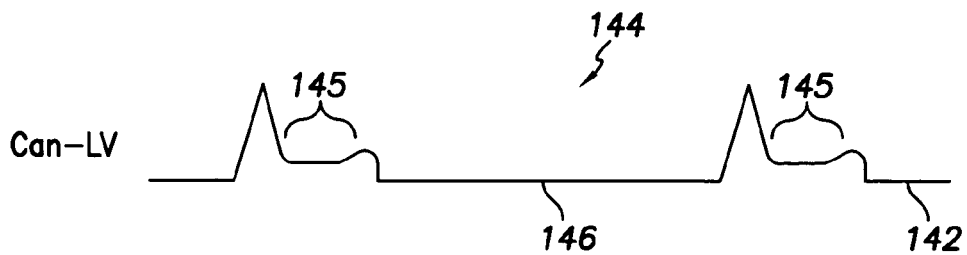
FIG. 13 is an EGM signal resulting from the left ventricular MI as sensed between a left ventricular electrode and the conductive enclosure of the device.

As previously mentioned, the difference in diagnostic capability of the sensing electrode configurations contemplated in accordance with this embodiment is illustrated in FIGS. 11–13.

FIG. 11 is an electrogram signal resulting from a left ventricular myocardial infarction as sensed between a left ventricular electrode such as coil electrode 29 and a right atrial electrode such as the right atrial or SVC coil electrode 38. As will be noted in the electrogram 140 of FIG. 11, the ST segments 141 are clearly elevated with respect to the baseline 142. This results because the right atrial coil electrode 38 and left ventricular coil electrode 29, with respect to the left ventricular myocardial infarction, are "outside" of the heart enabling the elevation in the ST segment 141 to be clearly sensed.

FIG. 13 shows an electrogram 144 resulting from the left ventricular myocardial infarction being sensed between a left ventricular electrode such as left ventricular coil electrode 29 and the conductive enclosure or can 40 of the device. Again, the left ventricular coil electrode 29 is seen as being "outside" of the heart with respect to the left ventricular myocardial infarction as is the conductive enclosure electrode 40. As a result, the ST segments 145 of electrogram 144 are seen as being elevated with respect to the baseline 146.

In contrast to the above, FIG. 12 is an electrogram signal 142 resulting from the left ventricular myocardial infarction as sensed between a left ventricular electrode such as left ventricular coil electrode 29 and a right ventricular electrode such as right ventricular coil electrode 36. As may be seen in FIG. 12, the electrogram signal 142 may be interpreted as being almost normal as the ST segments 143 thereof are essentially at baseline 144. This is due to cancellation effects across the heart during a large infarct. Such cancellation effects and normal ST segments have been found in patients with a myocardial infarct due to electrode cancellation effects.

Figure 14:
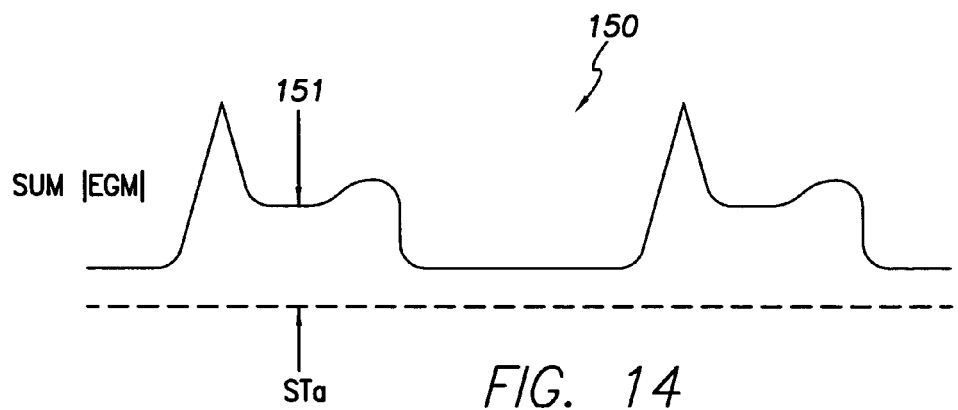
FIG. 14 is an EGM resulting from summing the absolute values of the EGM signals of FIGS. 11–13.
Figure 15:
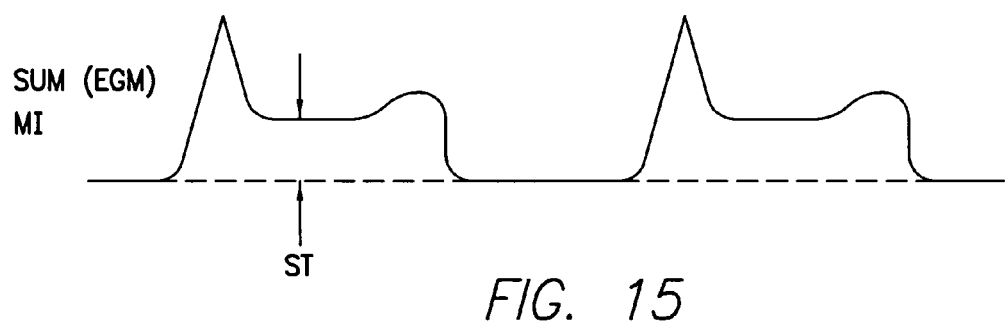
FIG. 15 is an EGM resulting from summing the actual values of the EGM signals of FIGS. 11–13 and the left ventricular MI.
Figure 16:
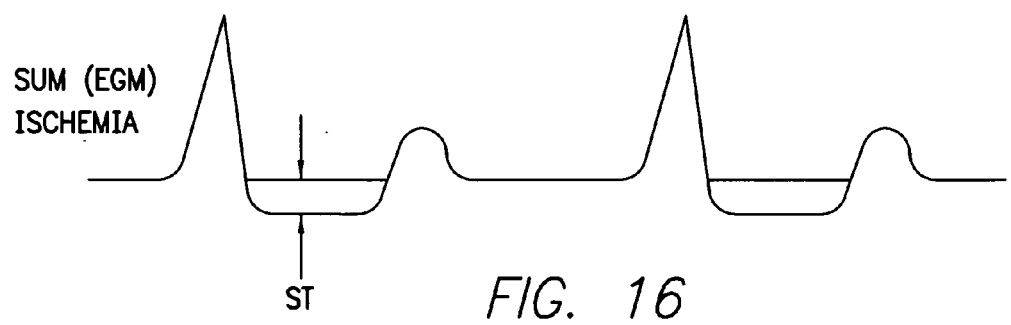
FIG. 16 is a representative EGM resulting from summing the EGM signals which would result from a left ventricular ischemia sensed with the sensing electrode configuration of FIGS. 11–13.

The electrograms of FIGS. 14–16 will be discussed during the description of the flow diagram of FIG. 17. Referring now to the flow diagram of FIG. 17, it describes an overview of the operation of one illustrative embodiment. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device.

Those skilled in the art may readily write such a control program based on the flow charts and other descriptions presented herein.

Figure 17:
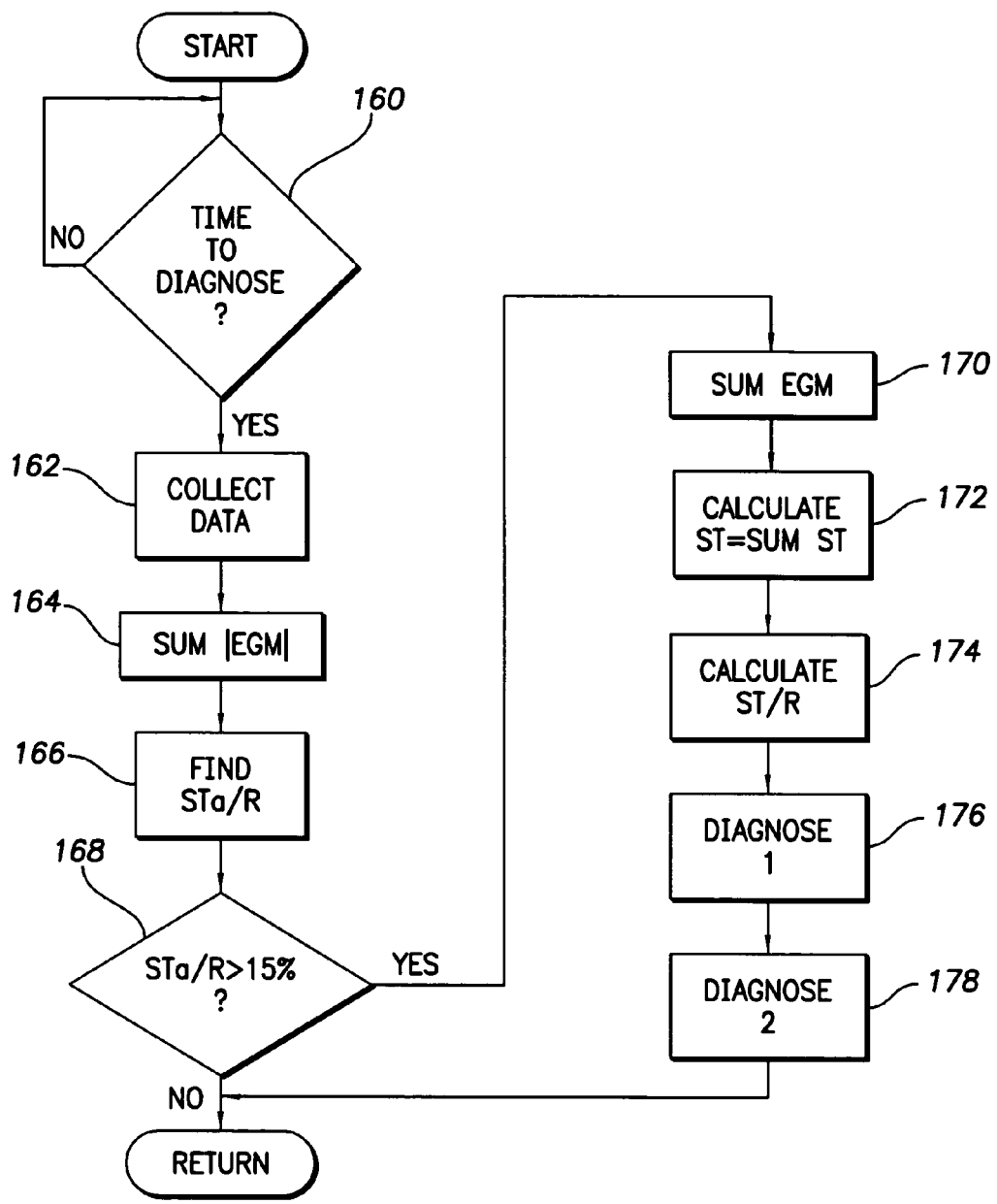
FIG. 17 is a flow chart describing an overview of the operation of one illustrative embodiment.

The overall process of FIG. 17 initiates with a decision block 160 wherein it is determined if it is time to detect for and potentially diagnose ischemia or myocardial infarction. Such detections may be taken frequently or less frequently as a patient's condition warrants. For example, it may be advantageous to implement a detection as often as, for example, every 10 minutes, or, as infrequently as once per day. The time interval between detections may be a programmable parameter set by the physician during the programming of the device.

If it is not time to detect for ischemia and myocardial infarction, the process returns. However, if it is time to detect and potentially diagnose ischemia or myocardial infarction, the process then advances to activity block 162 wherein electrogram data is collected. Here, electrograms are generated from a plurality of electrode configurations as, for example, the electrode configurations previously mentioned herein. These configurations include a left ventricular electrode to right atrial electrode, a left ventricular electrode to a right ventricular electrode, and the device conductive case to a left ventricular electrode. Again, the electrodes may be coil electrodes as previously described.

Once the electrograms are collected, the process advances to activity block 164. Here, the absolute value of the three electrograms are summed by, for example, the summer 62 of FIG. 2. If there is a myocardial infarction as previously illustrated with respect to FIGS. 11–13, a summed electrogram 150 may result when the absolute value of electrograms 140, 142, and 144 are summed. In the summing of the electrograms, a morphology detector 161 of the device 10 and as may be seen in FIG. 2 can be utilized to align the electrograms for summation, in a manner known in the art. Once the absolute value of the electrograms are summed, the morphology detector 161 may then be utilized to find the absolute value of the summed ST segments. This is illustrated at 151 of FIG. 14. Once the absolute value of the summed ST segments is found, that value, in accordance with activity block 166, may be divided by the amplitude of an R wave of the electrograms, to normalize the ST segment absolute value. The R wave selected may be the maximum R wave of the electrograms. Once the ST segment absolute value has been determined and normalized, the normalized value of the ST segment absolute value may then be used to determine if further analysis is required. Since the absolute value of the electrograms have been summed, the summed value will respond equally to ST segment depressions and ST segments elevations. As a result, if the normalized value of the absolute ST segment value is greater than a predetermined value, for example, 15%, this would indicate that there is an ST abnormality requiring further analysis. This step is indicated as decision block 168 of FIG. 17. If the normalized value is less than the predetermined value, the process returns. However, if it is greater than the predetermined value, this means that there is an ST abnormality and hence a potential ischemia or myocardial infarction to be detected.

Hence, the process will advance to activity block 170 wherein the electrograms are once again summed. Here, however, the electrograms are summed without taking their absolute value. FIG. 15 shows an illustrative summed EGM resulting from a myocardial infarct and FIG. 16 shows an illustrative summed EGM resulting from an ischemia condition. Next, the morphology detector 161 in accordance with activity block 172 determines the value of the summed ST segments of the electrograms. Next, the divider 67, in activity block 174, divides the summed ST segment value by an R wave amplitude to provide a normalized ST segment value. Once the normalized ST segment value is determined, the process advances to the first diagnosis subroutine 176. When the first diagnosis subroutine 176 is completed, the process then advances to the second or secondary diagnosis subroutine 178. When the second diagnosis subroutine is completed, the process returns.

Figure 18:
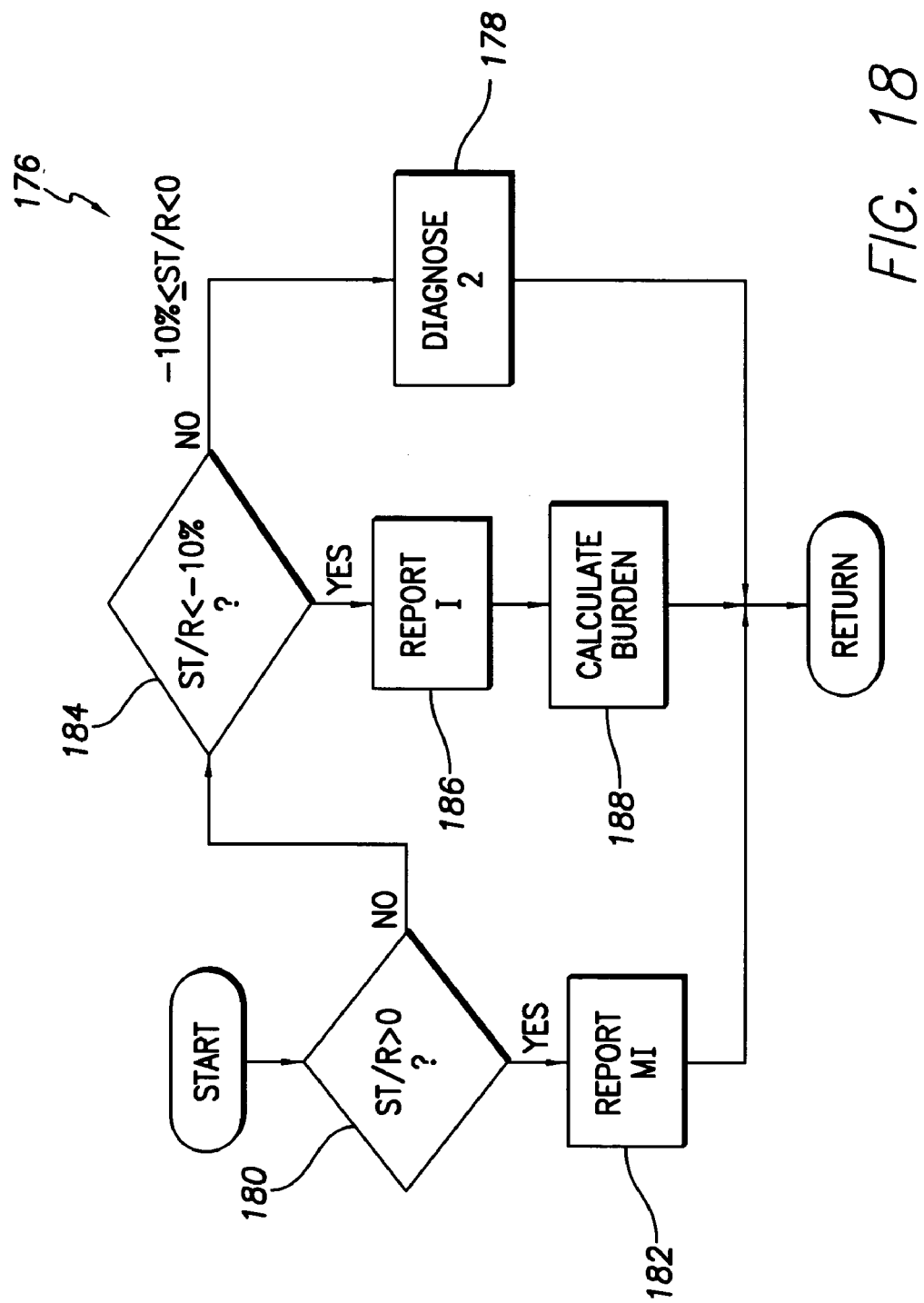
FIG. 18 is a flow chart describing the operation of a primary ischemia and MI detection subroutine according to this embodiment.

Referring now to FIG. 18, it shows a flowchart describing the first diagnosis subroutine 176 of FIG. 17. Here it will be seen that the first diagnosis discriminates between ischemia, myocardial infarction, and an equivocal condition.

First, the subroutine initiates at decision block 180 where it is determined if the normalized ST segment value is greater than zero. If it is greater than zero, this corresponds to an ST segment elevation and the determination that there is a myocardial ischemia. Hence, the process will immediately advance to activity block 182 to report a myocardial infarct.

If the normalized ST segment value is not greater than zero, the process will then advance to decision block 184 wherein it is determined if the normalized ST segment value is less than a second value as, for example, −10%. If it is, indicating an ST segment depression, ischemia will have been diagnosed and the process advances to activity block 186 to report the ischemic condition. Once the ischemic condition is reported, the process advances to activity block 188 to calculate a meaningful ischemia burden. The ischemia burden may be, for example, the ST segment normalized value multiplied by the ischemia duration providing a "area under the curve" indication of ischemia severity and time. The multiplication may be performed by the multiplier 65 of FIG. 2. The second burden may simply be the number of hours which ischemia is diagnosed. Hence, it is contemplated herein that a log is kept of the various diagnoses whether they be myocardial infarction, ischemia, or an equivocal condition and its resulting diagnosis.

If the normalized ST segment value is not greater than a first value of, for example, zero, or less than a second value of, for example, −10%, an equivocal condition will be diagnosed and the process will be advanced to the second diagnosis subroutine 178. Of course, as indicated in FIG. 18, after a myocardial infarction is reported in accordance with activity block 182 or after the ischemia burden is calculated in accordance with activity block 188 or after the second diagnosis subroutine 178 is completed, the process returns.

Figure 19:
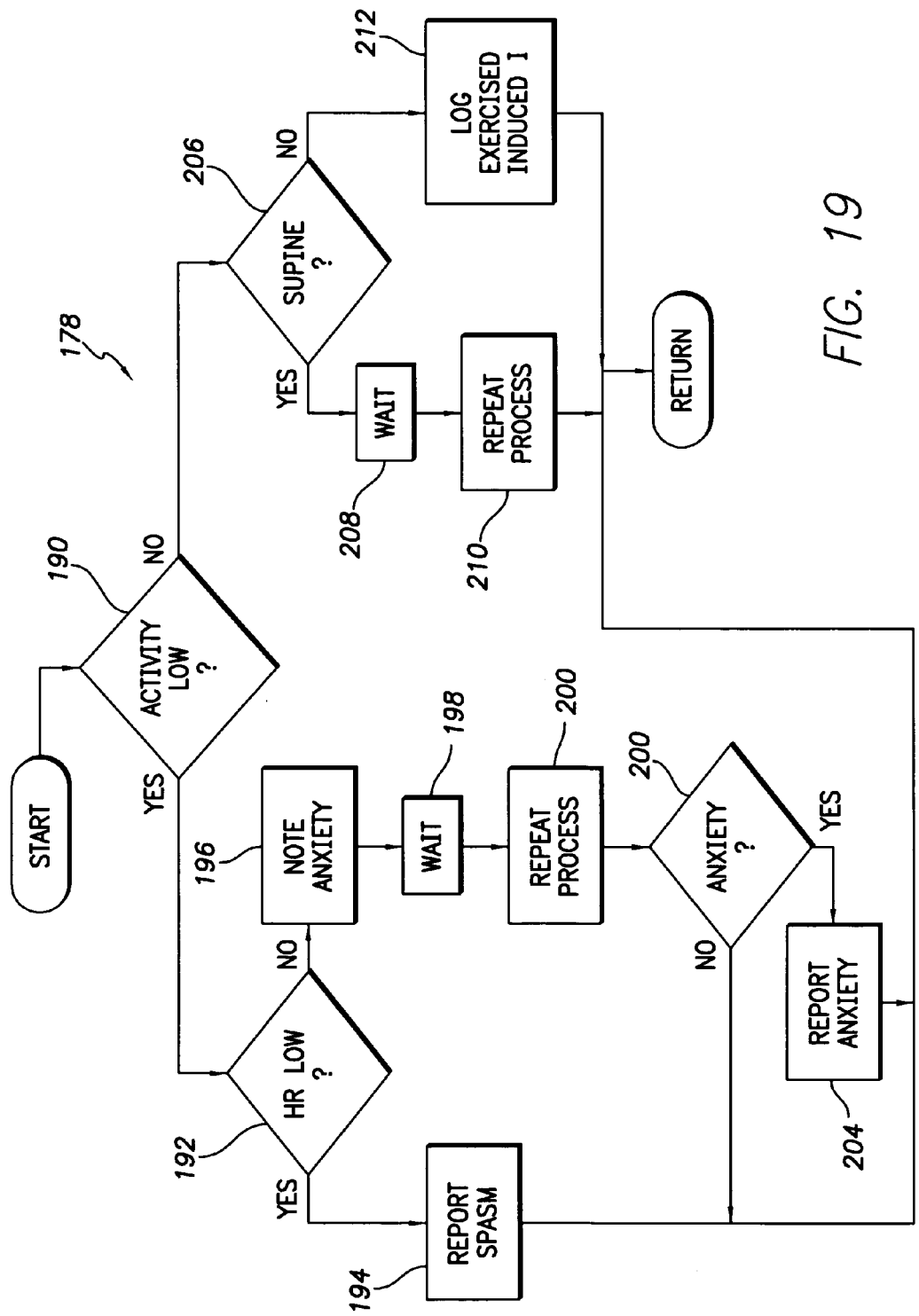
FIG. 19 is a flow chart describing the operation of a secondary diagnosis subroutine according to one illustrative embodiment.

Referring now to FIG. 19, it illustrates the secondary analysis 178 which is performed when an equivocal condition is diagnosed during the first diagnosis subroutine 176 of FIG. 18. The process of FIG. 19 initiates with decision block 190 wherein it is determined if the patient's activity is low. Here, the physiologic sensor 108 of FIG. 2 is utilized to provide a raw activity signal to the processor 60 to determine if the activity level of the patient is low. If the activity of the patient is low, the process advances to decision block 192 where it is determined if the patient's heart rate is low. This may be determined by the timing control 79 of FIG. 2. If the heart rate of the patient is low, a spasm is diagnosed and reported in accordance with activity block 194. The process then returns.

If in decision block 192 it is found that the heart rate is not low, then anxiety of the patient is noted in the log in accordance with activity block 196. The process then advances to activity block 198 wherein a wait period is timed. The wait period may be, for example, 10 minutes. Then, the process advances to activity block 200 wherein the process previously described is repeated. If during the repeated process it is determined that there is an equivocal condition, that the patient's activity is low, and that the patient's heart rate is not low, the process will then advance to decision block 202 to determine if the patient has previously experienced anxiety. If this is, for example, the second consecutive detection of anxiety, then the process advances to activity block 204 wherein anxiety of the patient is reported. This is most likely an anxiety reaction to chest pain. The process then returns. Of course, if it is found in decision block 202 that there is no anxiety, the process also returns at that time.

If in decision block 190 it is determined that the activity of the patient was not low, then the process advances to decision block 206 to determine if the patient is supine. This may be determined from the physiologic sensor 108. If it is determined that the patient is supine, the process advances to activity block 208 where another wait time of, for example, 10 minutes, is timed. The process then advances to activity block 210 to initiate repeat of the detection process and then returns.

However, if in decision block 206, it is determined that the patient is upright and not supine, the process advances to activity block 212 wherein an exercised induced ischemia is diagnosed and logged in memory 94. This may be retrieved later by the physician but is not a condition which must be immediately reported. The process then returns.

As can be seen from the foregoing, the illustrative embodiments provide a device and method that determines the presence of ischemia or myocardial infarction and discriminates between ischemia and myocardial infarction. In accordance with certain embodiments, the device discriminates between ischemia, myocardial infarction, and equivocal conditions of spasm, anxiety, and exercised induced ischemia. Hence, since myocardial infarction may be individually detected, patients will receive treatment for myocardial infarction in a much more timely manner than heretofore possible.

While specific embodiments and applications have been described, it is understood that numerous modifications and variations may be made thereto by those skilled in the art. It is therefore to be understood that within the scope of the claims, the invention may be practiced otherwise than as specifically described herein.

What is claimed is:

1. An implantable device that detects and discriminates between ischemia and myocardial infarction of a patient's heart, the device comprising:
   a plurality of electrodes that provide a plurality of cardiac activity sensing electrode configurations;
   a sensing circuit that provides a plurality of electrograms in response to cardiac activity sensed by the electrode configurations;
   a summer that provides a sum of the absolute value of the electrograms;
   a divider that divides the electrogram absolute value sum by an amplitude of one of the electrograms to provide a normalized value; and
   a discriminator that detects myocardial infarction and ischemia when the normalized value exceeds a predetermined value.

2. The device of claim 1 wherein the amplitude of one of the electrograms is an R wave amplitude.

3. An implantable device that detects and discriminates between ischemia and myocardial infarction of a patient's heart, the device comprising:
   a plurality of electrodes that provide a plurality of cardiac activity sensing electrode configurations;
   a sensing circuit that provides a plurality of electrograms in response to cardiac activity sensed by the electrode configurations;
   a summer that provides a sum of ST segments of the electrograms;
   a divider that provides a normalized ST segment value from the ST segment sum; and
   a discriminator that detects myocardial infarction when the normalized ST segment value is greater than a first value and detects ischemia when the normalized ST segment value is less than a second value.

4. An implantable device that detects and discriminates between ischemia and myocardial infarction of a patient's heart, the device comprising:
   a plurality of electrodes that provide a plurality of cardiac activity sensing electrode configurations;
   a sensing circuit that provides a plurality of electrograms in response to cardiac activity sensed by the electrode configurations;
   an arithmetic logic unit that provides an electrogram value of the electrograms; and
   a discriminator that detects myocardial infarction when the electrogram value is greater than a first value, ischemia when the electrogram value is less than a second value, and an equivocal condition when the electrogram value is between the first and second values.

5. The device of claim 4 wherein the discriminator provides a secondary analysis in response to detecting an equivocal condition.

6. The device of claim 5 wherein the discriminator determines at least one of patient heart rate, physical activity, and posture during the secondary analysis.

7. An implantable device that detects and discriminates between ischemia and myocardial infarction of a patient's heart, the device comprising:
   a plurality of electrodes that provide a plurality of cardiac activity sensing electrode configurations;
   a sensing circuit that provides a plurality of electrograms in response to cardiac activity sensed by the electrode configurations;
   a discriminator that discriminates between an ischemic condition of the heart, a myocardial infarcted condition of the heart, and an equivocal condition of the heart responsive to ST segments of the plurality of electrograms, and in response to detecting an equivocal condition, determines at least one of patient heart rate, physical activity, and posture and detects and discriminates between spasm, anxiety, and exercise induced ischemia.

8. The device of claim 7 wherein the discriminator determines an ischemia burden responsive to detecting ischemia.

9. The device of claim 8 wherein the ischemia burden is proportional to ischemia duration.

10. An implantable device that discriminates between ischemia and myocardial infarction of a patient's heart, the device comprising:
    a plurality of electrodes that provide a plurality of sensing electrode configurations;
    a sensing circuit that senses cardiac activity detected by the plurality of sensing electrode configurations to provide a plurality of cardiac activity signals; and
    a discriminator that combines corresponding phases from the plurality of cardiac activity signals to obtain a phase value and detects myocardial infarction when the phase value is greater than a first value, ischemia when the phase value is less than a second value, and an equivocal condition when the phase value is between the first and second values.

11. The implantable device of claim 10, wherein the corresponding phases comprise ST segments of the cardiac activity from the plurality of sensing electrode configurations.

12. A method of discriminating between ischemia and myocardial infarction of a patient's heart, the method comprising:
sensing cardiac activity of the heart with a plurality of cardiac activity sensing electrode configurations to provide a plurality of signals;
combining corresponding phases from the plurality of signals to obtain a phase value;
comparing the phase value to a first value and a second value; and
detecting myocardial infarction when the phase value is greater than the first value, ischemia when the phase value is less than the second value, and an equivocal condition when the phase value is between the first and second values.

13. The method of claim 12 further comprising determining an ischemia burden responsive to detecting ischemia.

14. The method of claim 12 further comprising conducting a secondary diagnosis responsive to detecting the equivocal condition.

15. The method of claim 14 wherein the secondary diagnosis includes determining at least one of heart rate, physical activity, and posture of the patient.

16. The method of claim 12 wherein the corresponding phases comprise ST segments and the phase value obtained comprises an ST segment value.

17. The method of claim 16 wherein comparing comprises detecting a myocardial infarction based on a positive ST segment value with respect to a baseline, and detecting ischemia based on a negative ST segment value with respect to a baseline.

18. A method comprising:
sensing cardiac activity of the heart with a plurality of cardiac activity sensing electrode configurations to provide a plurality of electrograms;
obtaining an electrogram value of the electrograms;
comparing the electrogram value to a first value and a second value; and
detecting myocardial infarction when the electrogram value is greater than the first value, ischemia when the electrogram value is less than the second value, and an equivocal condition when the electrogram value is between the first and second values.

* * * * *